United States Patent
Kim

(10) Patent No.: US 11,844,423 B2
(45) Date of Patent: Dec. 19, 2023

(54) ELECTRIC TOOTHBRUSH

(71) Applicant: Proxihealthcare Inc., Seoul (KR)

(72) Inventor: Young Wook Kim, Seoul (KR)

(73) Assignee: Proxihealthcare Inc., Seoul (KR)

( * ) Notice: Subject to any disclaimer, the term of this patent is extended or adjusted under 35 U.S.C. 154(b) by 604 days.

(21) Appl. No.: 17/003,142

(22) Filed: Aug. 26, 2020

(65) Prior Publication Data

US 2021/0307500 A1    Oct. 7, 2021

(30) Foreign Application Priority Data

Apr. 6, 2020 (KR) .................. 10-2020-0041386

(51) Int. Cl.
    *A46B 15/00*     (2006.01)
    *A46B 13/02*     (2006.01)
    *A61C 17/34*     (2006.01)

(52) U.S. Cl.
CPC .......... *A46B 15/0022* (2013.01); *A46B 13/02* (2013.01); *A61C 17/3481* (2013.01); *A46B 2200/1066* (2013.01); *A61C 2204/002* (2013.01)

(58) Field of Classification Search
CPC .... A61C 17/34; A46B 15/0022; A46B 13/023
See application file for complete search history.

(56) References Cited

U.S. PATENT DOCUMENTS

2018/0255916 A1* 9/2018 Levi ................. A46B 15/004

FOREIGN PATENT DOCUMENTS

| JP | 03116118 U | 12/1991 | |
|---|---|---|---|
| JP | 2542412 Y2 | 7/1997 | |
| JP | 10-080324 A | 3/1998 | |
| KR | 10-1639314 B1 | 7/2016 | |
| WO | 2009/006760 A1 | 1/2009 | |
| WO | 2017/122883 A1 | 7/2017 | |
| WO | WO-2017216606 A1 * | 12/2017 | ......... A46B 15/0022 |

OTHER PUBLICATIONS

The circuitry blog direct current alternating current overlapping end of the appendix 3 direct current AC circuit circle, Jul. 16, 2018, https://mathphysics.tistory.com/389.

* cited by examiner

*Primary Examiner* — Shay Karls
(74) *Attorney, Agent, or Firm* — NKL Law; Jae Youn Kim

(57) ABSTRACT

Disclosed is an electric toothbrush including a head and a handle having a shape couplable to the head and configured to supply a driving voltage to the head according to a user's control. The head includes a toothbrush head in which bristles and first and second electrodes spaced apart from each other are disposed, a head body extending from the toothbrush head, first and second connection lines disposed in the head body and connected from the toothbrush head to the first and second electrodes respectively, a head cover configured to close an end of the head body, and first and second connection pins respectively connected to the first and second connection lines and having portions externally exposed through the head cover.

13 Claims, 17 Drawing Sheets

ELECTRIC TOOTHBRUSH

CROSS-REFERENCE TO RELATED APPLICATION

This application claims priority to and the benefit of Korean Patent Application No. 10-2020-0041386, filed on Apr. 6, 2020, the disclosure of which is incorporated herein by reference in its entirety.

BACKGROUND

1. Field of the Invention

The present disclosure relates to an electric toothbrush and, more particularly, to an electric toothbrush allowing dental plaque to be effectively removed.

2. Discussion of Related Art

Dental plaque is a sticky and transparent film which builds up on tooth surfaces. Numerous microbes (bacteria) residing in the mouth combine with a specific constituent of saliva to form dental plaque, and dental plaque is formed not only on teeth and surroundings thereof but also on dental prostheses, surroundings of orthodontic appliances, and dentures.

When dental plaque builds up in the form of a very thin and transparent film, internal microbes increase. Microbes in dental plaque increase in geometric progression using sugar which is supplied when food is taken, and the amount thereof is also increased. Acid materials generated by microbes in plaque melt the calcified structure of teeth to make cavities, and poisonous substances thereof cause gingivitis.

Dental plaque is not easily seen visually and mainly builds up in crevasses, between teeth, and in narrow gaps between teeth and gums. Since dental plaque in such a narrow space causes problems in teeth and surrounding tissue, it is important to remove plaque everywhere without missing any spots. However, it is difficult to remove such plaque with an existing toothbrush.

SUMMARY OF THE INVENTION

The present disclosure is directed to providing an electric toothbrush allowing dental plaque to be effectively removed.

The present disclosure is also directed to providing an electric toothbrush allowing tooth decay and periodontal diseases to be prevented by removing dental plaque.

According to an exemplary embodiment of the present disclosure, an electric toothbrush includes a head and a handle having a shape couplable to the head and configured to supply a driving voltage to the head according to a user's control. The head includes a toothbrush head in which bristles and a first electrode and a second electrode spaced apart from each other are disposed, a head body extending from the toothbrush head, first and second connection lines disposed in the head body and connected from the toothbrush head to the first and second electrodes respectively, a head cover configured to close an end of the head body, and first and second connection pins respectively connected to the first and second connection lines and having portions externally exposed through the head cover.

The head cover may include a pillar in which a fixing-pin accommodation hole is formed and first and second seating areas present on both sides of the pillar.

A first pinhole that the first connection pin passes through may be formed in the first seating area, a second pinhole that the second connection pin passes through may be formed in the second seating area, and an end portion of the first connection line and an end portion of the second connection line may be bent and seated in the first seating area and the second seating area, respectively.

At least one protrusion may be disposed around each of the first seating area and the second seating area.

The end portion of the first connection line and the end portion of the second connection line may be bent in opposite directions.

A first connection hole corresponding to the first pinhole may be formed in the end portion of the first connection line, and a second connection hole corresponding to the second pinhole may be formed in the end portion of the second connection line.

First and second guide grooves may be formed lengthwise in a longitudinal direction to guide the first and second connection lines, respectively.

The first and second electrodes may have a height of 0.1 mm to 3 mm on the basis of the toothbrush head.

The handle may include a battery, a switch configured to control power supply from the battery, a vibration motor, a circuit configured to generate the driving voltage using a voltage of the battery, first and second connection terminals configured to respectively come into contact with the first and second connection pins to transfer the driving voltage generated by the circuit to the head when the head and the handle are coupled, and a fixing pin formed to protrude so as to be fixedly coupled with the head.

The driving voltage generated by the circuit may be set to have a frequency of 1 KHz to 1,000 MHz.

The circuit may include a direct current (DC)-DC converter which receives the voltage of the battery, a signal generator configured to generate the driving voltage using an output voltage of the DC-DC converter, a filter configured to perform a filtering operation on the driving voltage generated by the signal generator, and a calibrator configured to calibrate the driving voltage supplied through the filter and output the calibrated voltage.

The handle may include an internal case including a battery accommodation unit in which the battery is placed, a vibration motor seat in which the vibration motor is seated, and a coupling unit in which the first and second connection terminals and the fixing pin are installed and a circuit board on which the circuit is mounted, which is present between the switch and the vibration motor, and which is fixedly installed in the internal case.

The electric toothbrush may further include an upper cover installed on the coupling unit of the internal case and formed of an insulating material, an external case configured to accommodate the internal case and having a switch-pressing area corresponding to the switch, and a battery cap coupled to one end of the external case to close the battery accommodation unit.

The driving voltage may be generated by superposing a direct current (DC) voltage having B volts onto an alternating current (AC) voltage having an amplitude of A volts.

A ratio of A to B may be set to 1:0.5 to 10.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Exemplary embodiments of the present disclosure will be illustrated in the accompanying drawings and described in detail below. However, this is not intended to limit the present disclosure to the exemplary embodiments disclosed herein, and it is to be understood that the present disclosure can be implemented in various different forms and encompasses all modifications, equivalents, and substitutes included in the spirit and technical scope of the present disclosure.

Terms, such as "first," "second," "A," "B," "(a)," and "(b)," may be used to describe various elements. These terms are used only to distinguish one element from another, and the essences, sequences, orders, etc. of the elements are not limited by the terms. In addition, when an element is described as being "connected," "coupled," or "linked" to another element, it should be understood that the element may be connected or coupled directly to the other element or still another element may be "connected," "coupled," or "linked" between the elements. "Connection, "coupling," or "linkage" may be understood not only as physical "connection, "coupling," or "linkage" but also as electrical "connection," "coupling," or "linkage" as necessary.

Hereinafter, an electric toothbrush according to exemplary embodiments of the present disclosure will be described with reference to drawings related to the exemplary embodiments of the present disclosure.

Figure 1:
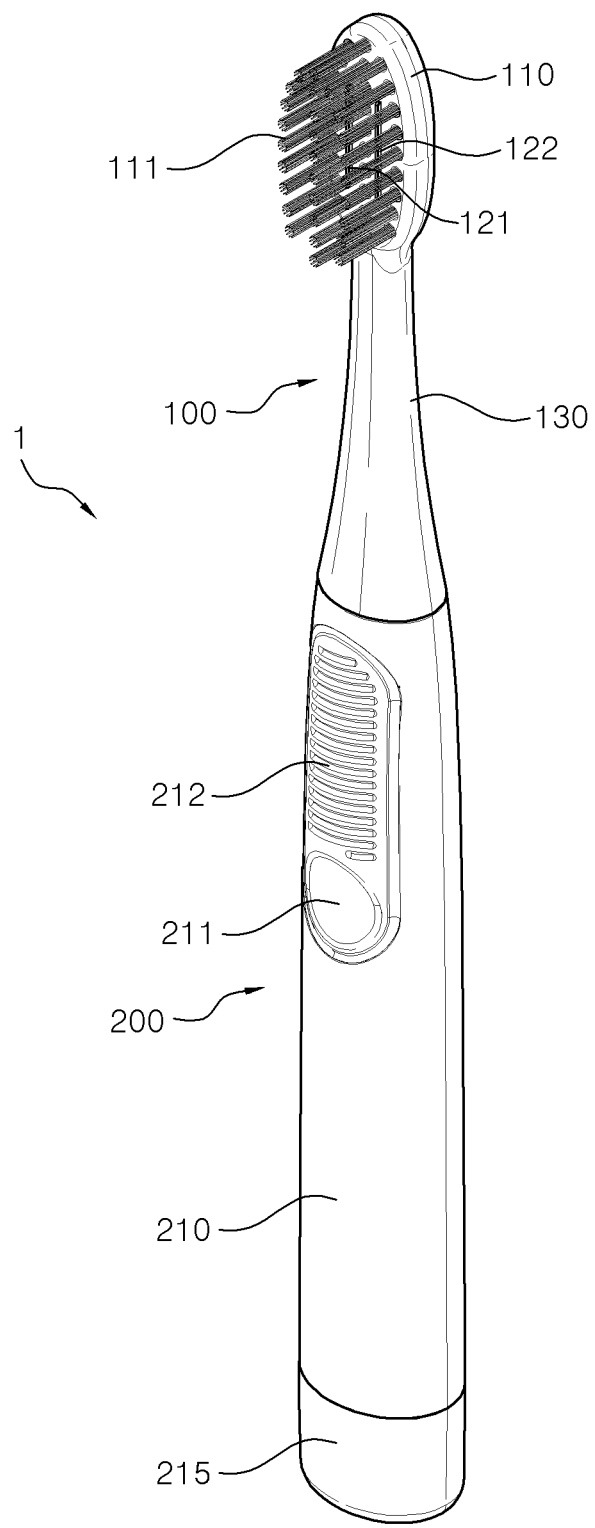
FIG. 1 is a view of an electrical toothbrush according to an exemplary embodiment of the present disclosure.
Figure 2:
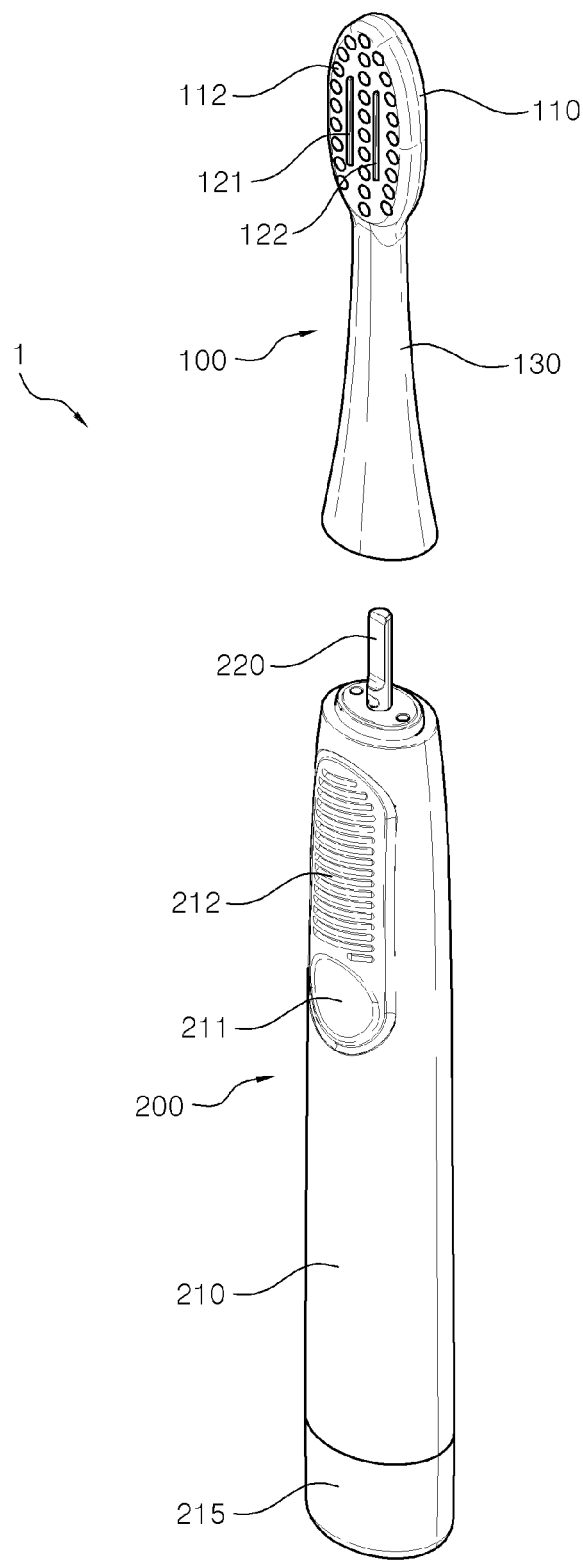
FIG. 2 is a view illustrating a separated state of the electrical toothbrush of FIG. 1.

FIG. 1 is a view of an electrical toothbrush according to an exemplary embodiment of the present disclosure, and FIG. 2 is a view illustrating a separated state of the electrical toothbrush of FIG. 1.

Referring to FIGS. 1 and 2, an electric toothbrush 1 according to the exemplary embodiment of the present disclosure may include a head 100 and a handle 200.

The head 100 may include a toothbrush head 110 and a head body 130 and may be designed to be separable from the handle 200.

Accordingly, when it is necessary to replace the head 100 due to aging or the like, a user may conveniently change the existing head 100 for a new head 100.

In the toothbrush head 100, toothbrush bristles 111, a first electrode 121, and a second electrode 122 may be disposed.

The toothbrush bristles 111 may be inserted into and fixed in multiple transplant holes 112 formed in the surface of the toothbrush head 110. The arrangement, number, size, etc. of the toothbrush bristles 111 are not particularly limited and may vary diversely.

The first electrode 121 and the second electrode 122 may be disposed apart from each other on the surface of the toothbrush head 110 and may be disposed to be coplanar with the toothbrush bristles 111.

The first electrode 121 and the second electrode 122 may form an electric field on the basis of electric energy supplied from the handle 200. Such an electric field may weaken the structure of dental plaque, and thus the user can effectively remove the dental plaque in his or her mouth using the electric toothbrush 1.

The head body 130 may extend from the toothbrush head 110 and constitute the body of the head 100. The head body 130 may be designed with a length suitable for use, and an end of the head body 130 may be coupled to the handle 200.

The handle 200 is the body of the electric toothbrush 1 and may be designed in a form which may be held when used by the user.

Also, the handle 200 may be coupled to the head 100 and may have a fixing pin 220 to be fixedly coupled with the head 100.

A battery 310 (see FIG. 7B) for power supply may be accommodated in the handle 200, and a battery cap 215 for replacement and the like of the battery 310 may be provided in the handle 200.

In addition, the handle 200 may have an external case 210 for accommodating and protecting internal components, and a switch-pressing area 211 and an anti-slip unit 212 may be formed on the external case 210.

The switch-pressing area 211 may be formed at a position corresponding to a switch 330 (see FIG. 7A) disposed in the handle 200, and the user can turn the internal switch 330 on or off by pressing the switch-pressing area 211.

To brush his or her teeth, the user may turn on the power of the electric toothbrush 1 by pressing the switch-pressing area 211. Accordingly, a driving voltage generated by the handle 200 is supplied to the first electrode 121 and/or the second electrode 122 of the head 100 so that an electric field may be generated to remove dental plaque.

The anti-slip unit 212 is intended to give the user a feeling of stable grip and may be designed with a structure and a material for increasing frictional force. For example, the anti-slip unit 212 may include multiple grooves.

Figure 3:
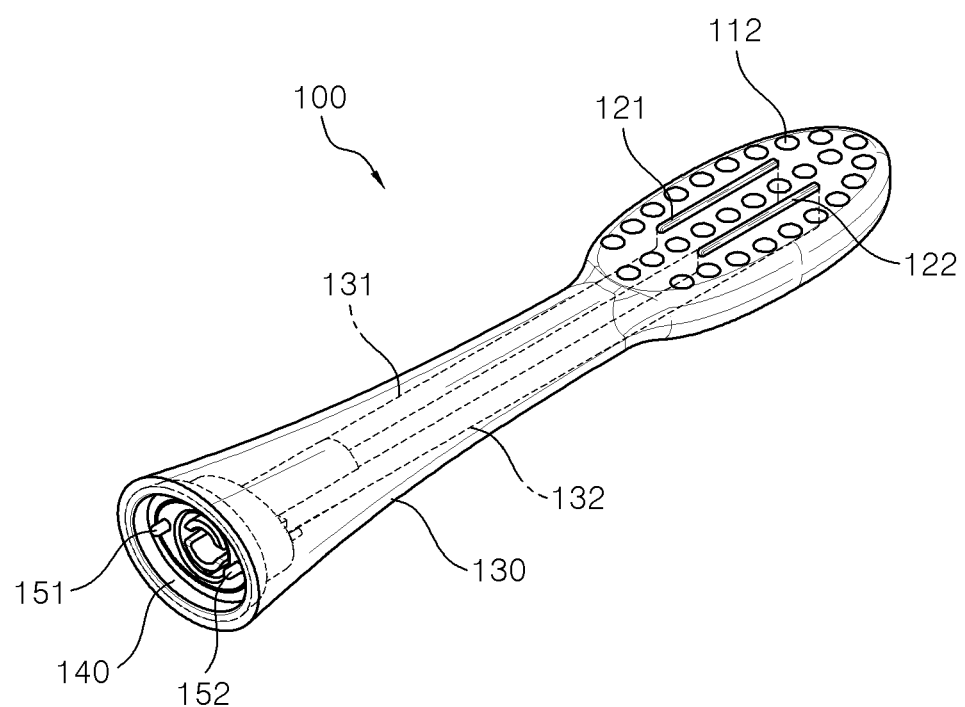
FIG. 3 is a view illustrating a head according to the exemplary embodiment of the present disclosure.
Figure 4A:
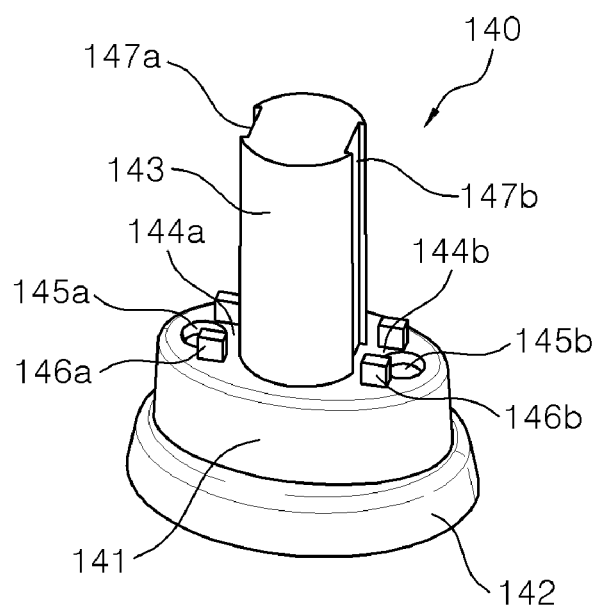
FIGS. 4A to 4C are views illustrating a head cover according to the exemplary embodiment of the present disclosure.
Figure 4B:
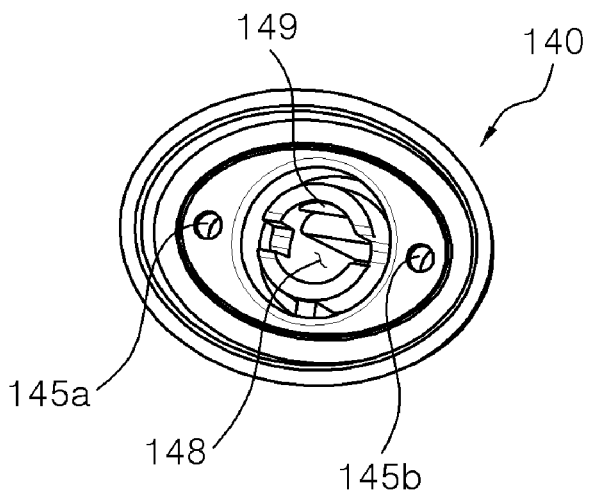
Figure 4C:
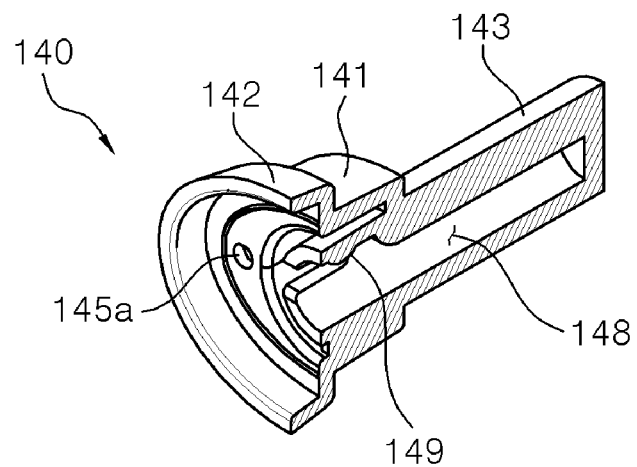
Figure 5A:
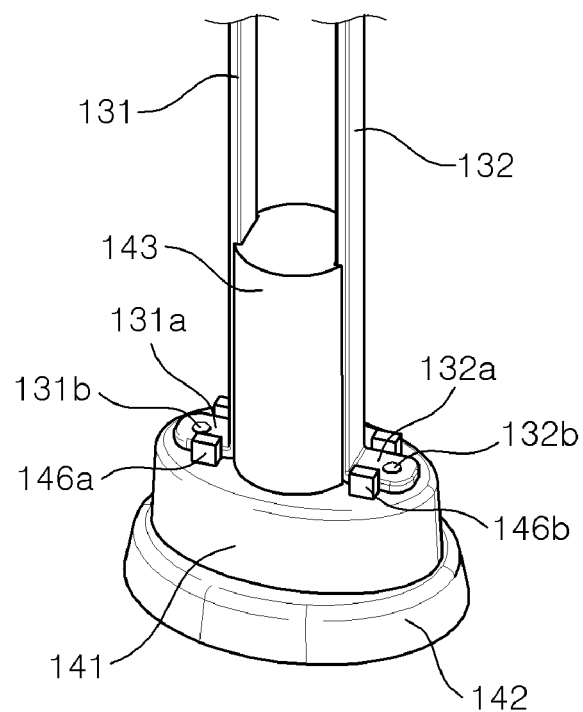
FIGS. 5A and 5B are views illustrating coupling between the head cover, connection lines, and connection pins according to the exemplary embodiment of the present disclosure.
Figure 5B:
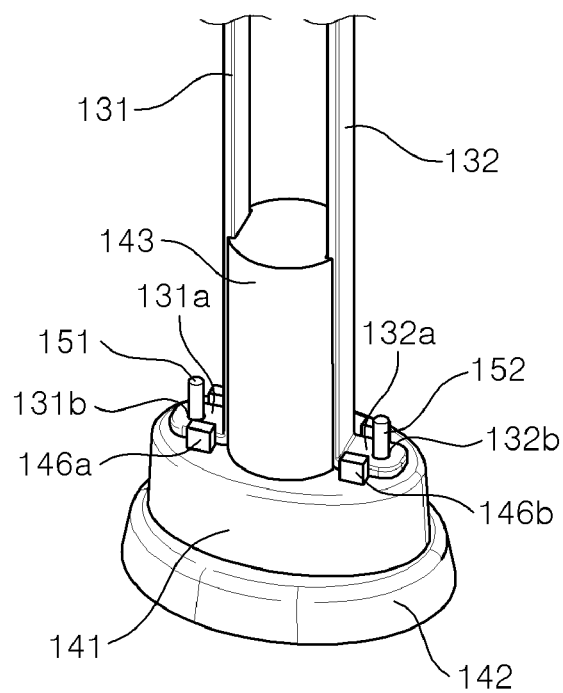
Figure 6:
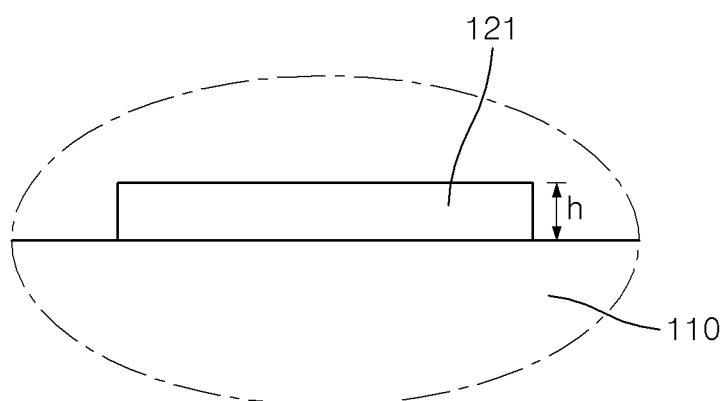
FIG. 6 is a diagram illustrating the height of an electrode according to the exemplary embodiment of the present disclosure.

FIG. 3 is a view illustrating the head according to the exemplary embodiment of the present disclosure, and FIGS. 4A to 4C show the head cover according to the exemplary embodiment of the present disclosure. FIGS. 5A and 5B are views illustrating coupling between the head cover, connection lines, and connection pins according to the exemplary embodiment of the present disclosure, and FIG. 6 is a diagram illustrating the height of an electrode according to the exemplary embodiment of the present disclosure.

In particular, FIG. 4A shows the head cover 140 seen from above, FIG. 4B shows the head cover 140 seen from below, and FIG. 4C shows a cross-section of the head cover 140.

Referring to FIG. 3, the head 100 according to the exemplary embodiment of the present disclosure may include the first electrode 121, the second electrode 122, the toothbrush head 110, the head body 130, a first connection line 131, a second connection line 132, the head cover 140, a first connection pin 151, and a second connection pin 152.

The first electrode 121 and the second electrode 122 may be disposed on the toothbrush head 110. For example, the first electrode 121 and the second electrode 122 may be set as a positive electrode and a negative electrode, respectively.

The first electrode 121 and the second electrode 122 may partially protrude from the toothbrush head 110. Referring to FIG. 6, the first electrode 121 may have a height h of 0.1 mm to 3 mm on the basis of the toothbrush head 110.

Also, the second electrode 122 may have the same height as the first electrode 121. For example, the second electrode 122 may have the height h of 0.1 mm to 3 mm on the basis of the toothbrush head 110.

When the height h of the electrodes 121 and 122 is set to less than 0.1 mm, the electrodes 121 and 122 may be buried in the toothbrush head 110 during a subsequent insert injection molding process. On the contrary, when the height h of the electrodes 121 and 122 is set to greater than 3 mm, the user may experience inconvenience due to the feeling of irritation, and damage may occur to teeth.

For example, the first electrode 121 and the second electrode 122 may be formed of brass, aluminum, conductive polymer, conductive silicon, stainless steel, or the like, but the material of the first and second electrodes 121 and 122 is not limited thereto. Any conductive material may be used as the electrode material.

The head body 130 may be integrally formed with the toothbrush head 110. For example, the head body 130 may be formed through insert injection molding like the toothbrush head 110.

In the head body 130, the first connection line 131 and the second connection line 132 may be disposed to transfer a driving voltage.

The first connection line 131 and the second connection line 132 may be connected to the first electrode 121 and the second electrode 122 in the toothbrush head 110, respectively. Also, the first connection line 131 and the second connection line 132 may extend toward the end of the head body 130 so as to be supplied with power from the handle 200 and may be electrically connected to the first connection pin 151 and the second connection pin 152 disposed in the head cover 140.

For convenience of manufacturing, the first connection line 131 and the first electrode 121 may be integrally formed, and the second connection line 132 and the second electrode 122 may also be integrally formed.

Also, the first connection line 131 and the second connection line 132 may be formed of the above-described electrode material.

The head cover 140 may be coupled to the head body 130 to close the end of the head body 130.

The first connection pin 151 and the second connection pin 152 may be connected to the first connection line 131 and the second connection line 132, respectively. A part of the first connection pin 151 and the second connection pin 152 may be externally exposed through the head cover 140.

When the head 100 and the handle 200 are coupled to each other later, the connection pins 151 and 152 may come into contact with connection terminals 361 and 362 (see FIG. 7A) disposed in the handle 200.

Referring to FIGS. 4A to 4C, the head cover 140 may include a pillar 143 in which a fixing-pin accommodation hole 148 is formed.

The fixing-pin accommodation hole 148 may be formed in the bottom surface of the head cover 140 and thereafter coupled to the fixing pin 220 of the handle 200.

Here, a convex portion 149 may be formed in the fixing-pin accommodation hole 148. When the fixing pin 220 is inserted into the fixing-pin accommodation hole 148, the convex portion 149 and a concave portion 222 (see FIG. 7C) of the fixing pin 220 may be coupled to each other to increase the force of coupling with the fixing pin 220.

Also, the pillar 143 may be disposed at the center of a first base 141 and extend upward. A first seating area 144a and a second seating area 144b may be present on both sides of the pillar 143.

Accordingly, the first seating area 144a and the second seating area 144b may be formed on the upper surface of the first base 141.

Also, one or more protrusions 146a and 146b may be disposed around the first seating area 144a and the second seating area 144b, respectively.

For example, at least one first protrusion 146a surrounding the first seating area 144a and at least one second protrusion 146b surrounding the second seating area 144b may be formed on the upper surface of the first base 141.

FIG. 4A shows a case in which two first protrusions 146a and two second protrusions 146b are formed. However, the present disclosure is not limited thereto, and the number of first protrusions 146a and the number of second protrusions 146b may vary diversely.

Due to the protrusions 146a and 146b, end portions 131a and 132a of the connection lines 131 and 132 may be stably seated in the seating areas 144a and 144b.

A first pinhole 145a may be formed in the first seating area 144a, and a second pinhole 145b may be formed in the second seating area 144b.

Therefore, the first connection pin 151 may pass the head cover 140 through the first pinhole 145a, and the second connection pin 152 may pass the head cover 140 through the second pinhole 145b.

Meanwhile, a first guide groove 147a and a second guide groove 147b may be formed in the pillar 143 lengthwise in the longitudinal direction to guide the first connection line 131 and the second connection line 132, respectively.

A second base 142 may be formed under the first base 141 with a larger diameter than that of the first base 141. However, the second base 142 may be omitted on the basis of necessity.

Referring to FIG. 5A, parts of the first connection line 131 and the second connection line 132 may be inserted into the first guide groove 147a and the second guide groove 147b of the pillar 143, respectively. The end portion 131a of the first connection line 131 and the end portion 132a of the second connection line 132 may be bent and seated in the first seating area 144a and the second seating area 144b, respectively.

In this case, the end portion 131a of the first connection line 131 and the end portion 132a of the second connection line 132 may be bent in opposite directions and may have a first connection hole 131b and a second connection hole 132b corresponding to the first pinhole 145a and the second pinhole 145b, respectively.

For example, the end portion 131a of the first connection line 131 is bent in a first direction and seated in the first seating area 144a, and accordingly, the first connection hole 131b formed in the end portion 131a may be present on the first pinhole 145a of the first seating area 144a.

Also, the end portion 132a of the second connection line 132 is bent in a second direction which is opposite to the first direction and seated in the second seating area 144b, and accordingly, the second connection hole 132b formed in the end portion 132a may be present on the second pinhole 145b of the second seating area 144b.

Referring to FIG. 5B, the first connection pin 151 may be disposed to pass through the first connection hole 131b of the first connection line 131 and the first pinhole 145a of the head cover 140, and the second connection pin 152 may be disposed to pass through the second connection hole 132b of the second connection line 132 and the second pinhole 145b of the head cover 140.

One end of the first connection pin 151 may be electrically connected to the end portion 131a of the first connection line 131 around the first connection hole 131b by a soldering process, and the other end of the first connection pin 151 may protrude downward through the first pinhole 145a of the head cover 140.

One end of the second connection pin 152 may be electrically connected to the end portion 132a of the second connection line 132 around the second connection hole 132b by a soldering process, and the other end of the second connection pin 152 may protrude downward through the second pinhole 145b of the head cover 140.

For example, the first connection pin 151 and the second connection pin 152 may be implemented as pogo pins in which springs are encapsulated.

After the assembly shown in FIG. 5B is finished, the toothbrush head 110 and the head body 130 may be formed through an insert injection molding process.

Figure 7A:
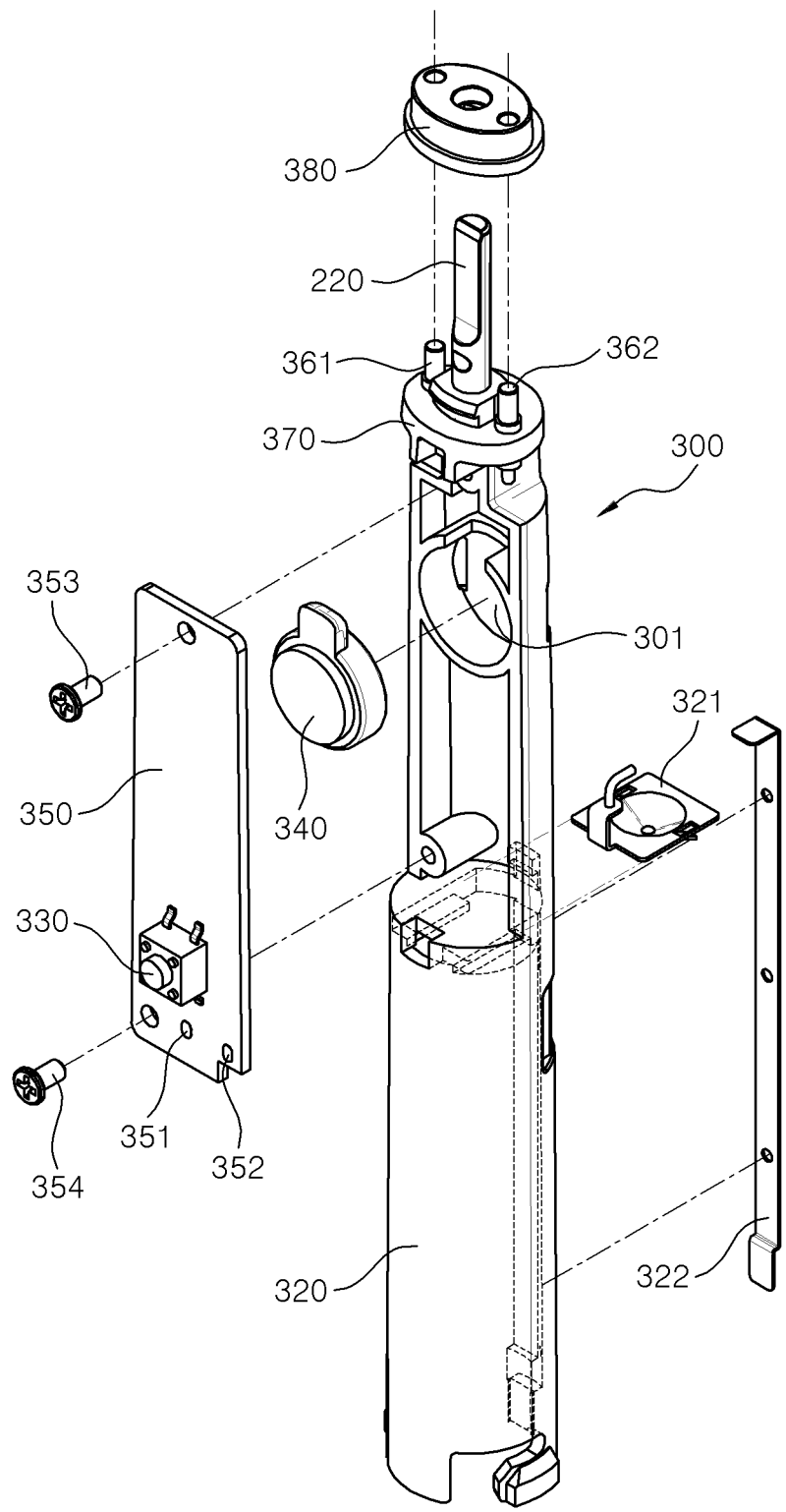
FIGS. 7A to 7C are an exploded view illustrating the internal configuration of a handle according to the exemplary embodiment of the present disclosure, a perspective view illustrating a coupled state of components shown in FIG. 7A, and a perspective view illustrating a fixing pin, connection terminals, etc. according to the exemplary embodiment of the present disclosure, respectively.
Figure 7B:
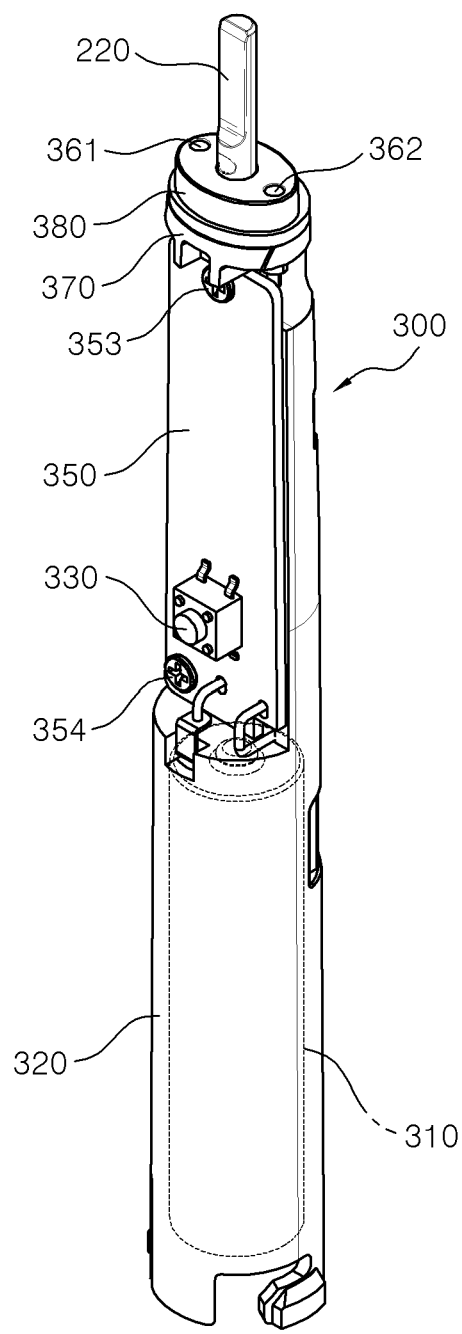
Figure 7C:
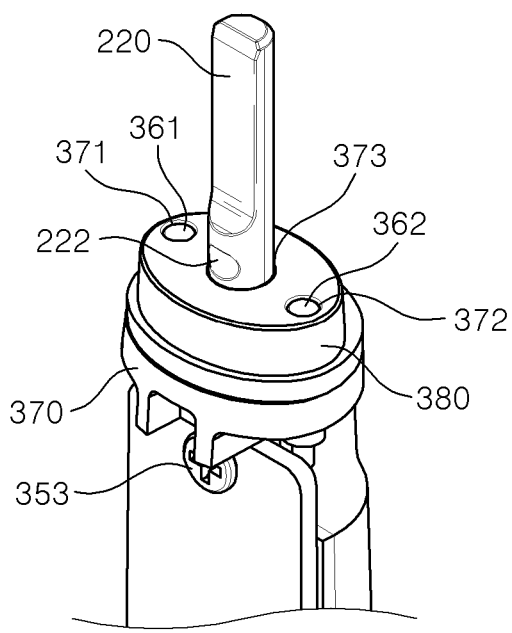

FIG. 7A is an exploded view illustrating the internal configuration of the handle according to the exemplary embodiment of the present disclosure, FIG. 7B is a perspective view illustrating a coupled state of components shown in FIG. 7A, and FIG. 7C is a perspective view illustrating the fixing pin, the connection terminals, etc. according to the exemplary embodiment of the present disclosure.

Referring to FIGS. 7A to 7C, the handle 200 according to the exemplary embodiment of the present disclosure may include the fixing pin 220, an internal case 300, the battery 310, the switch 330, a vibration motor 340, a circuit board 350, the first connection terminal 361, the second connection terminal 362, and an upper cover 380.

The internal case 300 is accommodated in the external case 210 and may provide an area and space in which components, such as the battery 310, the switch 330, the vibration motor 340, and the circuit board 350, are installed.

A battery accommodation unit 320 which accommodates the battery 310 is present in the lower portion of the internal case 300, and a vibration motor seat 301 in which the vibration motor 340 is seated may be provided above the battery accommodation unit 320. Also, in the upper portion of the internal case 300, a board-shaped coupling unit 370 in which the connection terminals 361 and 362 and the fixing pin 220 are installed may be formed.

A first battery terminal 321 and a second battery terminal 322 may be installed in the battery accommodation unit 320, and each of the first battery terminal 321 and the second battery terminal 322 may be electrically connected to the circuit board 350. For examples, the first battery terminal 321 may be connected to a first board terminal 351 of the circuit board 350, and the second battery terminal 322 may be connected to a second board terminal 352 of the circuit board 350.

The battery 310 may be inserted in the battery accommodation unit 320 and electrically connected to the battery terminals 321 and 322.

For example, the battery 310 may be a primary battery or a secondary battery.

When the battery 310 is a primary battery, the user may periodically change the batteries 310, and when the battery 310 is a secondary battery, the battery 310 may be charged through various charging methods.

For example, the battery 310 may be charged through a wireless charging method while present in the battery accommodation unit 320, or the battery 310 may be separated from the battery accommodation unit 320 and charged through a separate charging device.

The switch 330 is intended to control power supply from the battery 310 and may be installed on the circuit board 350.

The vibration motor 340 may be disposed in the vibration motor seat 301 provided in the internal case 300 and may provide vibrations to notify the user that the electric toothbrush 1 is operating.

For example, when the switch 330 is turned on by the user, the vibration motor 340 may start operation and continuously provide vibrations until the switch 330 is turned off. However, an operating method of the vibration motor 340 is not limited thereto, and a vibration pattern, vibration strength, etc. of the vibration motor 340 may be variously set.

The circuit board 350 may be fixedly installed in the internal case 300 by fastening members 353 and 354 and the like and may be disposed between the switch 330 and the vibration motor 340. Accordingly, the switch 330 may be disposed on the upper surface of the circuit board 350, and the vibration motor 340 may be disposed on the lower surface of the circuit board 350.

Also, a circuit 400 (see FIG. 10) which generates a driving voltage using the voltage of the battery 310 may be mounted on the circuit board 350.

The circuit 400 may generate the driving voltage using the voltage of the battery 310 which is supplied when the switch 330 is turned on. Also, the circuit 400 may provide a voltage required for operation of the vibration motor 340 to the vibration motor 340.

Each of the first connection terminal 361 and the second connection terminal 362 may be disposed to pass through the coupling unit 370. When the head 100 is coupled to the handle 200, the first connection terminal 361 and the second connection terminal 362 may respectively come into contact with the first connection pin 151 and the second connection pin 152 of the head 100 to transfer the driving voltage generated by the circuit 400 to the head 100.

To this end, lower ends of the connection terminals 361 and 362 protruding downward from the coupling unit 370 may be connected to the circuit board 350 on which the circuit 400 is mounted, and upper ends of the connection terminals 361 and 362 protruding upward from the coupling unit 370 may be externally exposed through the upper cover 380.

The fixing pin 220 may be disposed at the center of the coupling unit 370 and extend upward lengthwise and may be inserted into and coupled to the fixing-pin accommodation hole 148 provided in the head 100. As described above, the concave portion 222 corresponding to the convex portion 149 of the fixing-pin accommodation hole 148 may be formed on the fixing pin 220.

The upper cover 380 may be installed on the coupling unit 370 of the internal case 300 and formed of an insulating material such as silicone.

The upper cover 380 may have a first opening 371 for externally exposing the first connection terminal 361, a second opening 372 for externally exposing the second connection terminal 362, and a third opening 373 that the fixing pin 220 may pass through.

Figure 8:
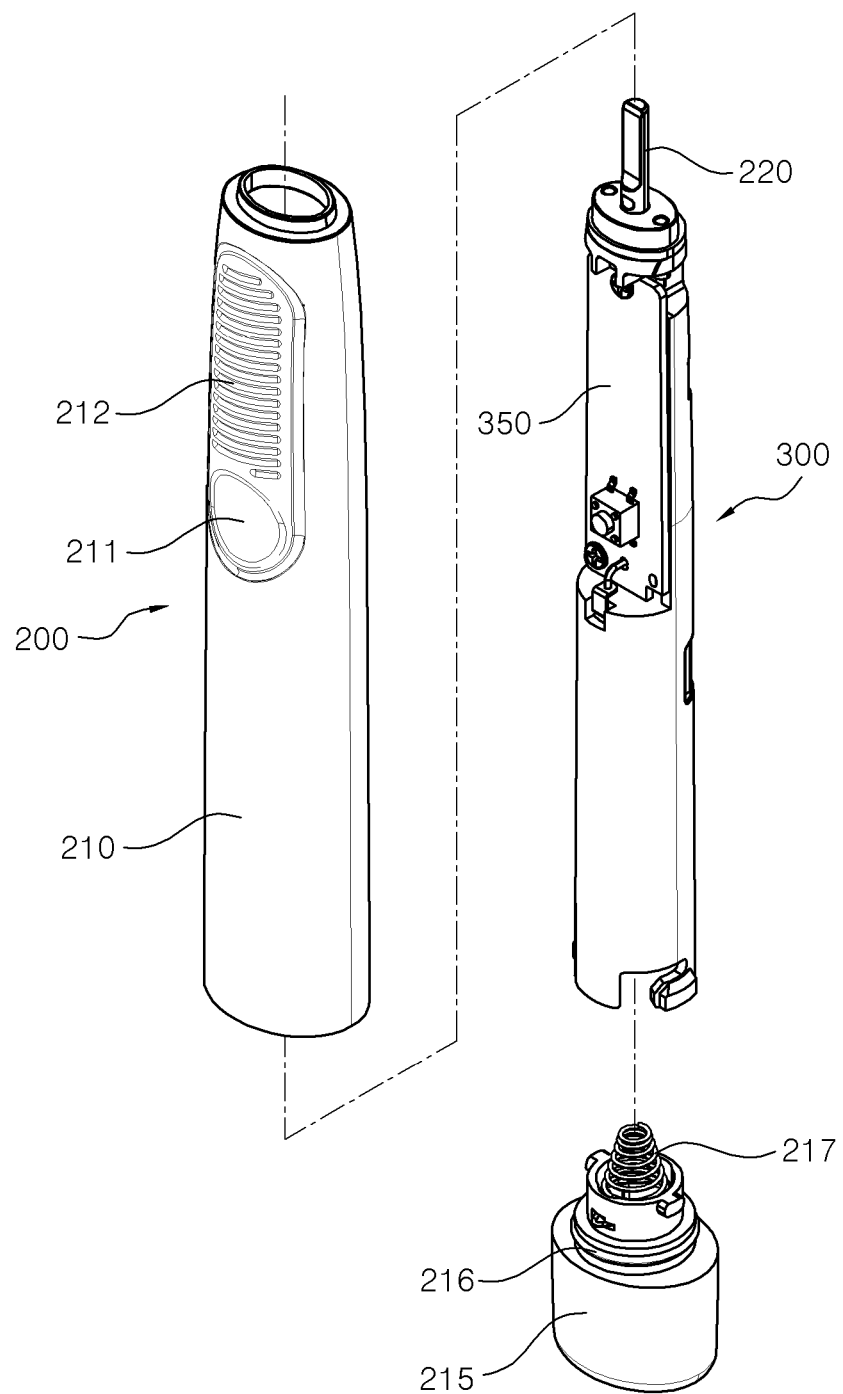
FIG. 8 is a perspective view illustrating coupling between a battery cap, an internal case, and an external case according to the exemplary embodiment of the present disclosure.

FIG. 8 is a perspective view illustrating coupling between the battery cap, the internal case, and the external case according to the exemplary embodiment of the present disclosure.

Referring to FIG. 8, the external case 210 may be installed outside the internal case 300 to which the switch 330, the vibration motor 340, the circuit board 350, etc. are coupled, and the battery cap 215 may be coupled to the lower portion of the internal and external cases 300 and 210.

In the battery cap 215, an O-ring 216 for sealing and a spring 217 electrically connected to the second battery terminal 322 may be installed.

Figure 9:
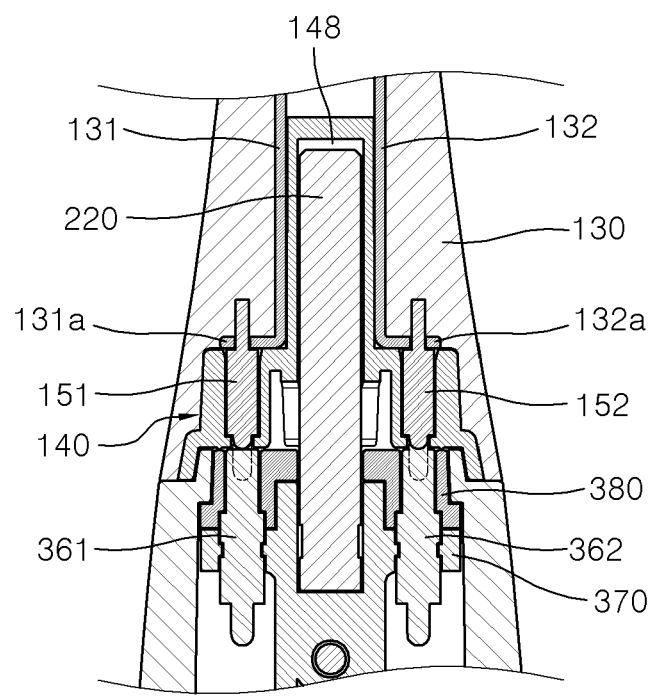
FIG. 9 is a partial cross-sectional view of the electric toothbrush when the head and the handle are coupled according to the exemplary embodiment of the present disclosure.

FIG. 9 is a partial cross-sectional view of the electric toothbrush when the head and the handle are coupled according to the exemplary embodiment of the present disclosure.

Referring to FIG. 9, when the head 100 and the handle 200 are coupled, the fixing pin 220 is inserted into and coupled to the fixing-pin accommodation hole 148. Also, the first connection pin 151 connected to the end portion 131*a* of the first connection line 131 may come into contact with the first connection terminal 361, and the second connection pin 152 connected to the end portion 132*a* of the second connection line 132 may come into contact with the second connection terminal 362.

After that, as the user presses the switch-pressing area 211, the internal switch 330 is turned on, and the circuit 400 may generate and supply the driving voltage to the first connection line 131 and the second connection line 132 through the circuit board 350 and the connection terminals 361 and 362. Accordingly, the first electrode 121 and the second electrode 122 may form an electric field for removing dental plaque on the basis of the supplied driving voltage.

Figure 10:
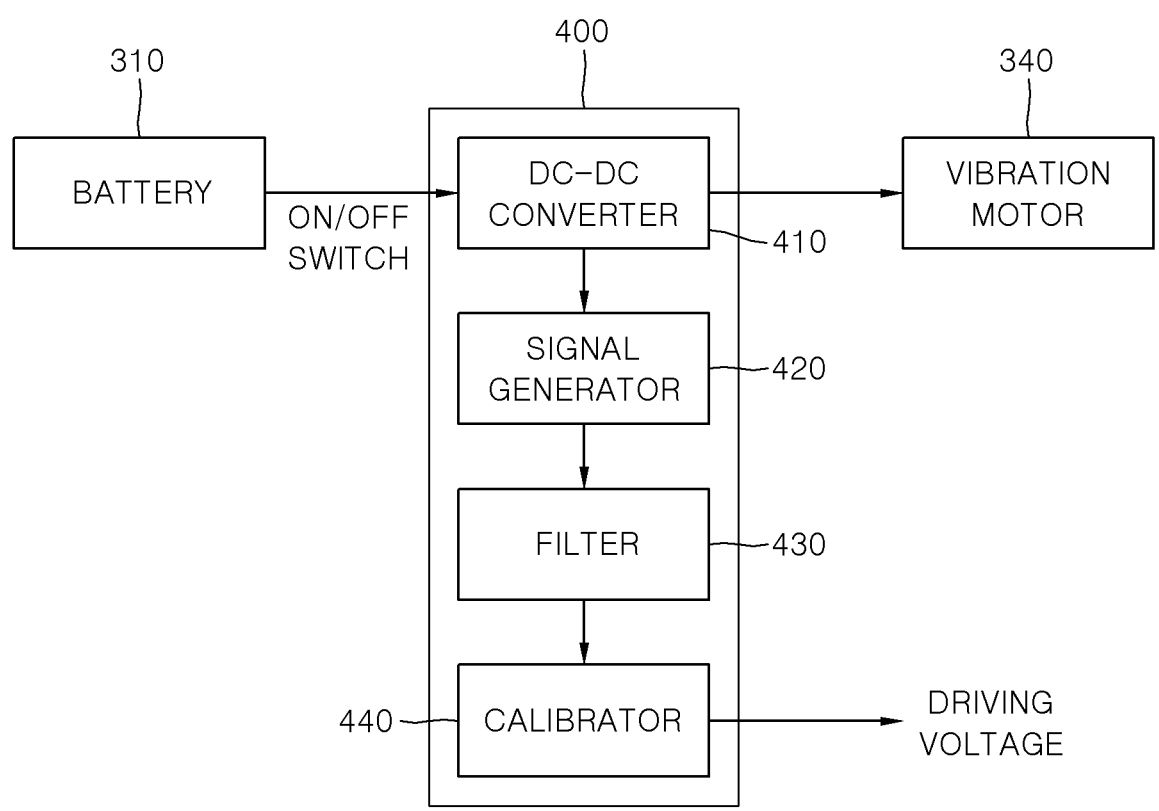
FIG. 10 is a block diagram of a circuit according to the exemplary embodiment of the present disclosure.
Figure 11A:
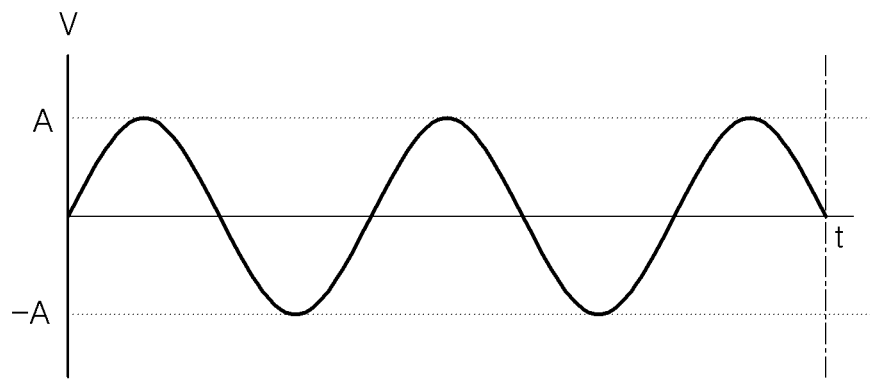
FIGS. 11A to 11C are graphs illustrating a driving voltage according to the exemplary embodiment of the present disclosure.
Figure 11B:
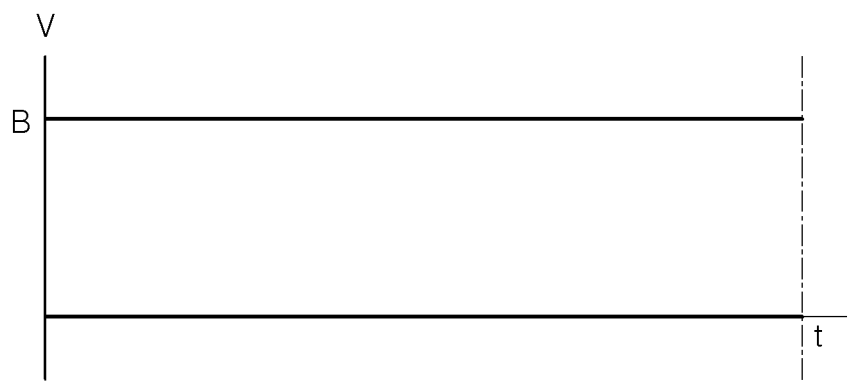
Figure 11C:
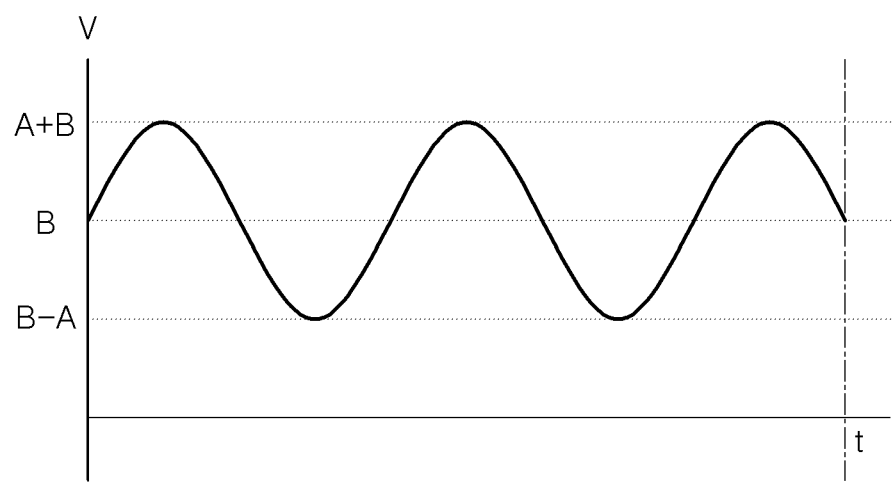

FIG. 10 is a block diagram of a circuit according to the exemplary embodiment of the present disclosure, and FIGS. 11A to 11C are graphs illustrating a driving voltage according to the exemplary embodiment of the present disclosure.

Referring to FIG. 10, the circuit 400 according to the exemplary embodiment of the present disclosure may include a direct current (DC)-DC converter 410, a signal generator 420, a filter 430, and a calibrator 440.

The DC-DC converter 410 may receive a voltage from the battery 310 and convert the voltage into a certain level of voltage. The voltage converted by the DC-DC converter 410 may be used as a voltage for driving the vibration motor 340.

For example, when the switch 330 is turned on, the DC-DC converter 410 may receive the battery voltage to operate, and when the switch 330 is turned off, the DC-DC converter 410 may stop operating.

The signal generator 420 may operate on the basis of the voltage supplied from the DC-DC converter 410 and generate the driving voltage using an output voltage of the DC-DC converter 410.

In this case, the driving voltage may be set to have a frequency of 1 KHz to 1,000 MHz. This is because the effects of removing dental plaque are degraded when the driving voltage is set to have a low frequency of less than 1 KHz and even when the driving voltage is set to have a ultra-high frequency of greater than 1,000 MHz. Meanwhile, the driving voltage may be set to have a frequency of 5 MHz to 15 MHz which is suitable for removing dental plaque.

The signal generator 420 may be implemented with a well-known device such as an oscillator or a function generator.

The filter 430 may perform a filtering operation on the driving voltage generated by the signal generator 420. For example, the filter 430 may include a low pass filter to convert a sawtooth-wave driving voltage into a sine wave form. However, the filter 430 is not limited to this type, and various filters may be employed according to a designed structure.

The calibrator 440 may calibrate the driving voltage supplied through the filter 430 and output the calibrated voltage.

In this case, the calibrator 440 may receive an alternating current (AC) driving voltage and calibrate an offset of the driving voltage by applying a DC voltage to the driving voltage.

Accordingly, the driving voltage may be generated by superposing the DC voltage onto the AC voltage.

The calibrator 440 may receive an AC voltage having an amplitude of A volts (V) as shown in FIG. 11A from the filter 430 and generate a final driving voltage as shown in FIG. 11C by superposing a DC voltage having B volts (V) as shown in FIG. 11B onto the AC voltage.

In this case, a ratio of the amplitude A of the AC voltage to the voltage value B of the DC voltage may be set to 1:0.5 to 10.

For example, when the amplitude A of the AC voltage is set to 0.2 V to 0.3 V, the voltage value B of the DC voltage may be set to 0.1 V to 3.0 V.

Since the driving voltage is set in a form obtained by superposing the DC voltage onto the AC voltage as described above, it is possible to reduce the risk of an electric shock to the human body and pain which may be caused to the human body as compared with a case of applying only a DC voltage. However, the present disclosure is not limited thereto, and the driving voltage may only be a DC voltage or an AC voltage as necessary.

Although not shown in the drawings, a controller may be additionally installed in the circuit 400.

Meanwhile, the driving voltage supplied from the circuit 400 to the head 100 may be set to 0.1 mV to 3 V. When the driving voltage is less than 0.1 mV, it is difficult to remove plaque, and when the driving voltage exceeds 3 V, body fluids may be electrolyzed so that a toxic substance may be generated.

Also, the driving voltage may have a shape of a pulse wave, a square wave, a triangle wave, etc. in addition to a sine wave.

FIGS. 12A to 12E are diagrams illustrating electrode arrangements according to other exemplary embodiments of the present disclosure.

FIGS. 1, 2, etc. described above show the exemplary embodiment in which one first electrode 121 and one second electrode 122 are arranged in the vertical direction, but the arrangement of the first electrode 121 and the second electrode 122 may vary diversely.

Figure 12A:
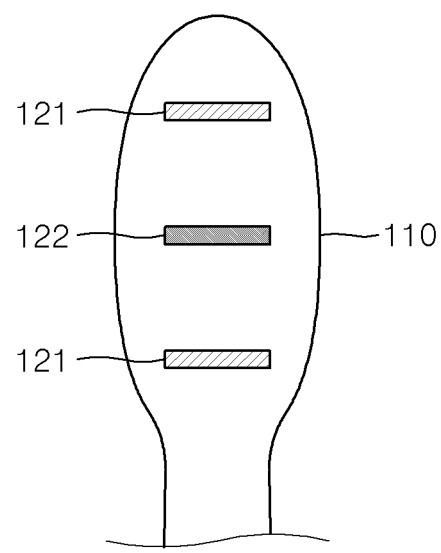
FIGS. 12A to 12E are diagrams illustrating electrode arrangements according to other exemplary embodiments of the present disclosure.

For example, as shown in FIG. 12A, the first electrode 121 and the second electrode 122 may be arranged in the horizontal direction, and the number of installed first electrodes 121 and second electrodes 122 may vary.

Figure 12B:
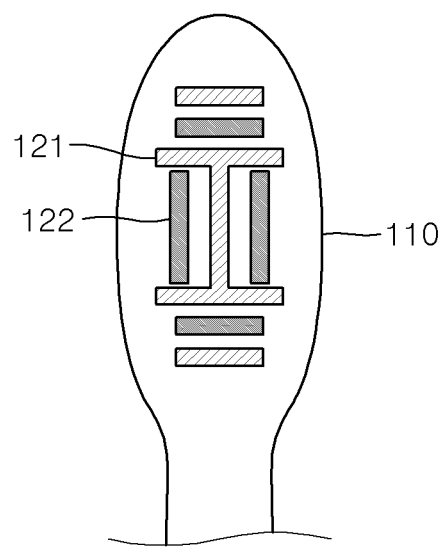

Also, as shown in FIG. 12B, an "I" shaped first electrode 121 may be disposed at the center of the toothbrush head 110, and a plurality of first electrodes 121 and second electrodes 122 having a straight-line shape may be arranged around the "I" shaped first electrode 121.

Figure 12C:
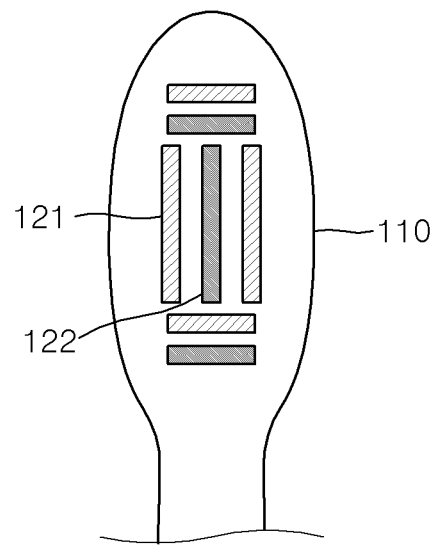

Referring to FIG. 12C, a plurality of first electrodes 121 may be arranged in a quadrangular shape on the toothbrush head 110, and a plurality of second electrodes 122 may be arranged between the first electrodes 121 or outside the first electrodes 121 on the toothbrush head 110.

Figure 12D:
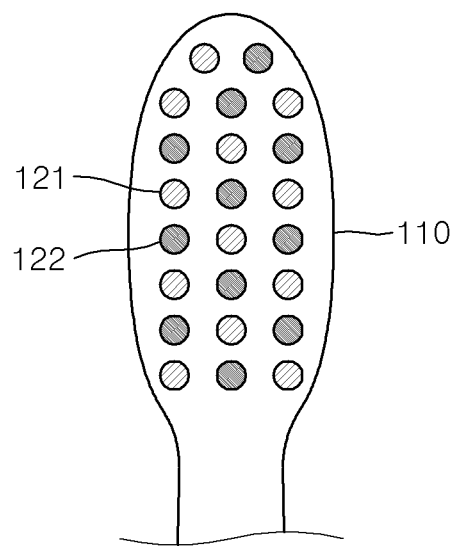

Referring to FIG. 12D, first electrodes 121 and second electrodes 122 may have a cylindrical shape, and multiple first electrodes 121 and multiple second electrodes 122 may be arranged on the toothbrush head 110.

Figure 12E:
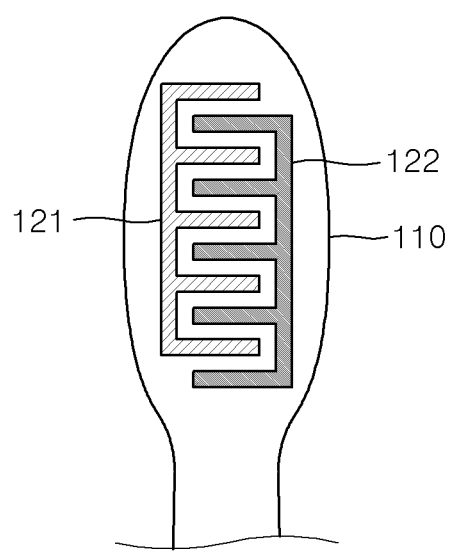

Referring to FIG. 12E, a first electrode 121 and a second electrode 122 may be formed in a sawtooth shape in which the first electrode 121 and the second electrode are engaged with each other.

Figure 13A:
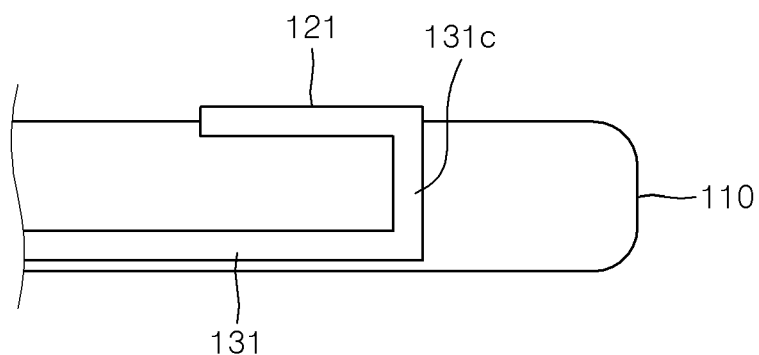
FIGS. 13A and 13B are diagrams illustrating a designed structure of a connection line and an electrode according to other exemplary embodiments of the present disclosure.
Figure 13B:
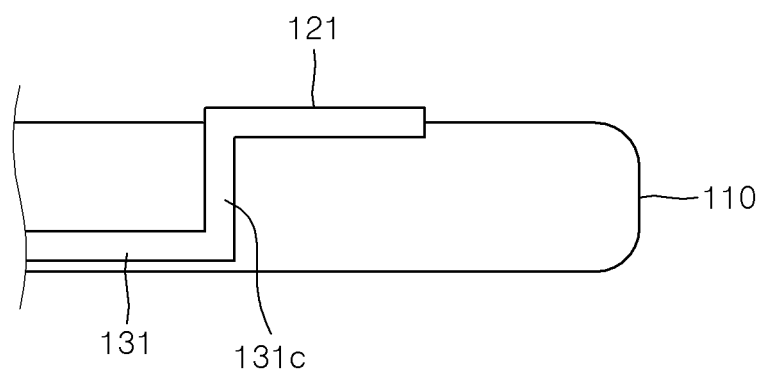

FIGS. 13A and 13B are diagrams illustrating a designed structure of a connection line and an electrode according to other exemplary embodiments of the present disclosure.

Referring to FIGS. 13A and 13B, an end portion 131c of the first connection line 131 may be bent upward and connected to the first electrode 121.

In this case, compared with the shape shown in FIG. 3, it is possible to reduce a required amount of the electrode material, and thus the cost can be reduced.

Although not shown in the drawings, an end portion of the second connection line 132 may also be bent upward and connected to the second electrode 122 in the same shape as the end portion of the first connection line 131.

According to the above-described present disclosure, it is possible to provide an electric toothbrush allowing dental plaque to be effectively removed.

According to the present disclosure, it is also possible to provide an electric toothbrush allowing tooth decay and periodontal diseases to be prevented by removing dental plaque.

Those of ordinary skill in the art can appreciate that it is possible to implement the present disclosure in another specific form without changing the technical spirit or essential characteristics of the present disclosure. Accordingly, it should be understood that the embodiments described above are merely exemplary and are not limiting. The scope of the present disclosure is defined by the appended claims to be described below, rather than the above detailed description. It should be appreciated that all modifications or variations derived from the meaning and scope of the appended claims and their equivalents fall within the scope of the present disclosure.

What is claimed is:

1. An electric toothbrush comprising:
a head; and
a handle having a shape couplable to the head and configured to supply a driving voltage to the head according to a user's control,
wherein the head comprises:
a toothbrush head in which bristles and a first electrode and a second electrode spaced apart from each other are disposed;
a head body extending from the toothbrush head;
a first connection line and a second connection line disposed in the head body and connected from the toothbrush head to the first electrode and the second electrode, respectively;
a head cover configured to close an end of the head body; and
a first connection pin and a second connection pin respectively connected to the first connection line and the second connection line and having portions externally exposed through the head cover,
wherein the head cover comprises:
a pillar in which a fixing-pin accommodation hole is formed; and
a first seating area and a second seating area present on both sides of the pillar,
wherein a first pinhole that the first connection pin passes through is formed in the first seating area,
a second pinhole that the second connection pin passes through is formed in the second seating area, and
an end portion of the first connection line and an end portion of the second connection line are bent and seated in the first seating area and the second seating area, respectively.

2. The electric toothbrush of claim 1, wherein at least one protrusion is disposed around each of the first seating area and the second seating area.

3. The electric toothbrush of claim 1, wherein the end portion of the first connection line and the end portion of the second connection line are bent in opposite directions.

4. The electric toothbrush of claim 3, wherein a first connection hole corresponding to the first pinhole is formed in the end portion of the first connection line, and
a second connection hole corresponding to the second pinhole is formed in the end portion of the second connection line.

5. The electric toothbrush of claim 1, wherein a first guide groove and a second guide groove are formed lengthwise in a longitudinal direction to guide the first connection line and the second connection line, respectively.

6. The electric toothbrush of claim 1, wherein the first electrode and the second electrode have a height of 0.1 mm to 3 mm on the basis of the toothbrush head.

7. The electric toothbrush of claim 1, wherein the handle comprises:
a battery;
a switch configured to control power supply from the battery;
a vibration motor;
a circuit configured to generate the driving voltage using a voltage of the battery;
a first connection terminal and a second connection terminal configured to respectively come into contact with the first connection pin and the second connection pin to transfer the driving voltage generated by the circuit to the head when the head and the handle are coupled; and
a fixing pin formed to protrude so as to be fixedly coupled with the head.

8. The electric toothbrush of claim 7, wherein the driving voltage generated by the circuit is set to have a frequency of 1 KHz to 1,000 MHz.

9. The electric toothbrush of claim 8, wherein the circuit comprises:

a direct current (DC)-DC converter which receives the voltage of the battery;

a signal generator configured to generate the driving voltage using an output voltage of the DC-DC converter;

a filter configured to perform a filtering operation on the driving voltage generated by the signal generator; and a calibrator configured to calibrate the driving voltage supplied through the filter and output the calibrated voltage.

10. The electric toothbrush of claim 7, wherein the handle comprises:

an internal case including a battery accommodation unit in which the battery is placed, a vibration motor seat in which the vibration motor is seated, and a coupling unit in which the first connection terminal, the second connection terminal, and the fixing pin are installed; and a circuit board on which the circuit is mounted, which is present between the switch and the vibration motor, and which is fixedly installed in the internal case.

11. The electric toothbrush of claim 10, further comprising:

an upper cover installed on the coupling unit of the internal case and formed of an insulating material;

an external case configured to accommodate the internal case and having a switch-pressing area corresponding to the switch; and a battery cap coupled to one end of the external case to close the battery accommodation unit.

12. The electric toothbrush of claim 1, wherein the driving voltage is generated by superposing a direct current (DC) voltage having B volts onto an alternating current (AC) voltage having an amplitude of A volts.

13. The electric toothbrush of claim 12, wherein a ratio of A to B is set to 1:0.5 to 10.

* * * * *